United States Patent [19]

Coakley et al.

[11] Patent Number: 5,425,921
[45] Date of Patent: Jun. 20, 1995

[54] SEALABLE VESSEL FOR CONTAINING AND PROCESSING ANALYTICAL SAMPLES

[75] Inventors: Joseph Coakley, Woodland; James Godsey, Folsom; David Sherman, Sacramento, all of Calif.

[73] Assignee: Dade International Inc., Deerfield, Ill.

[21] Appl. No.: 257,225

[22] Filed: Jun. 8, 1994

Related U.S. Application Data

[63] Continuation of Ser. No. 934,825, Aug. 24, 1992, abandoned.

[51] Int. Cl.⁶ .................................................. B01L 3/00
[52] U.S. Cl. ...................................... 422/102; 422/99; 422/100; 422/103; 436/174; 73/864.91; 220/400; 220/410; 222/548
[58] Field of Search ................ 422/99, 100, 102, 103; 73/864.91; 220/400, 410; 222/183, 548; 436/174

[56] References Cited

U.S. PATENT DOCUMENTS

| | | | |
|---|---|---|---|
| 2,961,228 | 11/1960 | Moore | 432/262 |
| 3,855,997 | 12/1974 | Sauer | 128/760 |
| 4,042,337 | 8/1977 | Griffith | 422/102 |
| 4,538,653 | 9/1985 | Shea et al. | 141/285 |
| 4,729,875 | 3/1988 | Chandler | 422/58 |
| 4,756,434 | 7/1988 | Frank | 215/201 |
| 4,769,333 | 9/1988 | Dole et al. | 435/287 |
| 4,775,629 | 10/1988 | Kuhl et al. | 222/548 X |
| 4,830,210 | 5/1989 | Mabille | 215/309 |
| 4,859,603 | 8/1989 | Dole et al. | 435/287 |
| 4,956,298 | 9/1990 | Diekmann | 422/102 X |
| 5,019,348 | 5/1991 | Ohms et al. | 422/63 |
| 5,100,025 | 3/1992 | McGraw | 222/183 X |
| 5,139,742 | 8/1992 | Heijink | 422/102 X |

FOREIGN PATENT DOCUMENTS

0482713A2 4/1992 European Pat. Off. .

*Primary Examiner*—James C. Housel
*Assistant Examiner*—Maureen M. Wallenhorst
*Attorney, Agent, or Firm*—Mark J. Buonaiuto

[57] ABSTRACT

A sealable container for holding an analytical sample for processing is disclosed. The container includes a body with a dispensing port and an insert member with an outlet port slidably received in the body. The insert member and the body are movable relative to each other between a first position, in which the outlet port is substantially aligned with the dispensing port, and a second position, in which the outlet port is substantially out of alignment with the dispensing port. Sealing between the insert member and the body, which may take the form of O-rings, provide a substantially airtight, hermetic seal between a reaction chamber formed in the insert member and the body so that the reaction chamber can be sealed or isolated from the outside environment. The container is particularly adapted to contain the processes of nucleic acid amplification and to thereby reduce the problems of sample cross-contamination encountered in such processes. A method of processing an analytical sample using such a container is also disclosed.

4 Claims, 4 Drawing Sheets

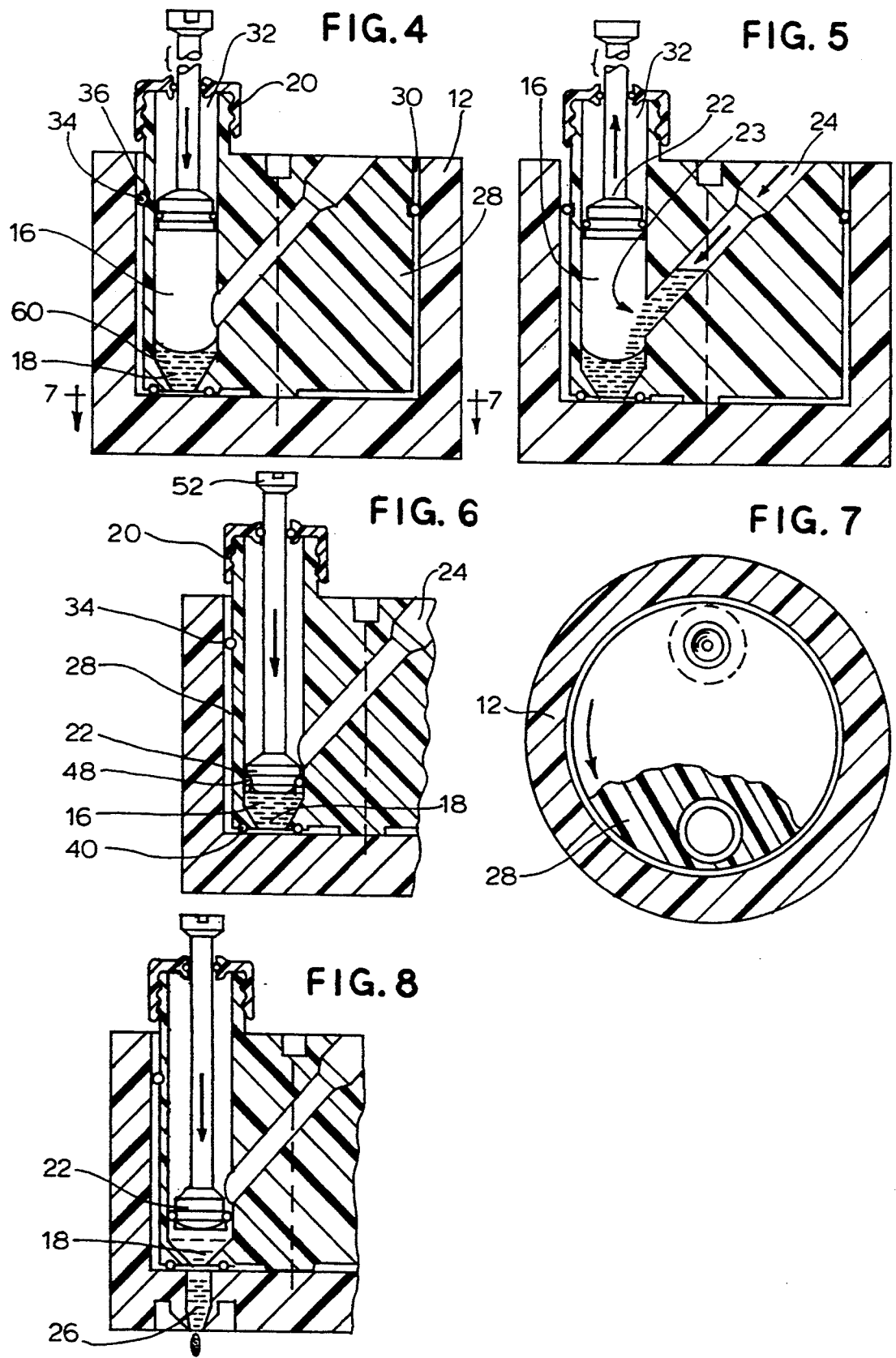

SEALABLE VESSEL FOR CONTAINING AND PROCESSING ANALYTICAL SAMPLES

This is a continuation of application Ser. No. 07/934,825, filed on Aug. 24, 1992, now abandoned.

FIELD OF THE INVENTION

This invention relates generally to containers for holding analytical samples and added reagents in a sealed environment, and is particularly directed to sealed vessels for containing the processes of target nucleic acid amplification in isolation from the outside environment.

BACKGROUND OF THE INVENTION

Modern medical diagnostic tests rely upon the isolation and identification of nucleic acid sequences. Nucleic acids are the components of the genetic material of organisms and are arranged sequentially in long strands to form molecules such as deoxyribonucleic acid (DNA) and ribonucleic acid (RNA). For example, in order to determine whether a patient is suffering from an illness associated with a particular virus, tests have been developed to identify one or more nucleic acid sequences unique to that virus. These tests rely on the fact that probes complementary to the target nucleic acid sequence will selectively bind or hybridize to the target sequence. The probe is chemically labelled so that it can be detected by one or more analytical methods, such as fluorometry. If a sample contains the target nucleic acid sequence, the probe will bind to the target and the presence of the bound probe can be used to confirm the presence of the target sequence.

Because the target molecule may be present in extremely small quantities in many test samples, processes have been developed to increase or "amplify" the number of nucleic acid copies present so that the target sequence can be more readily identified. Several methods of target amplification chemistry have been developed, including self-sustaining sequence replication ("3SR"), polymerase chain reaction ("PCR"), and the transcriptional amplification system ("TAS"), and several variations thereof. Basically, such methods produce copies of the nucleic acid in multiple reiterative steps such that the copies produce further copies in an exponential fashion. In this way, small amounts of nucleic acids can be rapidly amplified by a factor of more than one million, thereby producing sufficient quantities of target needed for detection in diagnostic tests. For a general discussion of amplification techniques, the reader is referred to U.S. Pat. No. 4,683,202 (Mullis), which is incorporated herein by reference and made a part hereof.

Although such target amplification procedures are extremely powerful, several drawbacks have arisen with their use. The most significant problem is so-called sample "cross-contamination," that is, the contamination of one sample with amplified target from previous amplification procedures. Reagents used in current amplification methods can also be contaminated in this manner. Because of the power and specificity of amplification techniques, even extremely small amounts of nucleic acid carried in aerosols created during normal laboratory procedures or present in trace amounts on laboratory equipment can contaminate a sample and result in false positive results, seriously jeopardizing the reliability of diagnostic tests. In extreme situations, contamination problems have become so severe and widespread that it has been necessary to relocate entire laboratories.

Laboratories have developed various methods to help minimize cross-contamination. One approach is to store separate, small aliquots of reagents and to dispense these reagents using so-called "positive displacement" pipettes, so that the reagents and sample do not contact the outside environment before or during the amplification reaction. Other approaches include physically separating amplification reactions from other laboratory processing steps and/or pre-treating reagents with ultraviolet light to destroy nucleic acid fragments present in the reagents as a result of contamination.

These techniques for preventing sample and reagent cross-contamination suffer from a number of drawbacks. Physical separation makes it more difficult to perform diagnostic procedures in a single instrument, since amplification must be confined to a separate area—or even a separate room—in the laboratory. Likewise, pretreatment with UV light does not guarantee that there will be no cross-contamination, since the reagents may potentially be exposed to contamination after such pretreatment but prior to amplification.

Chemical contamination control techniques are also known. Such techniques include so-called "pretreatment," in which DNA sequences are chemically modified during amplification. As a result, DNA copies made by amplification are chemically unique from the target. If these unique copies have contaminated a sample, they can be selectively destroyed prior to each new test without destroying the target. "Post-treatment" techniques are also known, in which the DNA strands are cross-linked after amplification, making them chemically incapable of being amplified.

Such chemical contamination control techniques also have drawbacks associated with their use. The principal drawback is that such techniques tend to reduce the sensitivity of detection, either by reducing the number of amplified copies or by rendering the amplified copies more difficult to detect with probes. Thus, the existence of these techniques does not eliminate the need for physical isolation of the amplification reaction, particularly when high sensitivity of detection is desired.

Containers for physically isolating analytical samples are also known. For example, U.S. Pat. No. 2,961,228 to Moore discloses a crucible to prevent a sample from exposure to the atmosphere prior to testing. However, this device is not adapted for use in modern diagnostic procedures and, in particular, procedures which involve nucleic acid amplification.

Accordingly, a need exists for an analytical sample container which can maintain the processes of target nucleic acid amplification (including sample lysing, addition of amplification reagents, and amplification) in substantial isolation from the outside environment, thereby helping to reduce sample and reagent cross-contamination. Further, a need exists for a sample container which permits the required amplification reagents to be added to the sample while still maintaining the sample in isolation from the outside environment. A need also exists for a container which may be used in a single, automated or semi-automated instrument, but which is relatively simple in design and easy to manufacture.

SUMMARY OF THE INVENTION

Accordingly, it is an object of the present invention to provide a sample container for clinical specimens which maintains the specimen and added reagents in isolation from the outside environment to prevent specimen and reagent cross-contamination, It is a further object of this invention to provide a sample container which is designed to permit the addition of reagents (and, preferably, the reagents required for nucleic acid amplification) while still maintaining the sample and reagents in isolation from the outside environment.

It is a further object of this invention to provide a sample container which is relatively simple in design and easy and inexpensive to manufacture so that the container may be disposed of after use, thereby further reducing contamination problems.

It is a further object of this invention to provide a sample container which is designed so that precise quantities of the sample and, when amplification is performed, amplified target, may be reliably dispensed from the container for further processing in diagnostic procedures.

It is a further object of this invention to provide a sample container which is adapted for use in an automated or semi-automated instrument.

It is a further object of this invention to provide a sample container which simplifies sample handling and processing.

It is a further object of this invention to provide a sample container made of materials which are capable of withstanding the varying temperature conditions used for many amplification reactions.

These and other objects are accomplished by providing a container for holding an analytical sample during processing which comprises a body with a dispensing port and an insert member slidably received in the body. The insert member defines a reaction chamber with an outlet port. The insert member and the body are movable relative to each other between a first position, in which the outlet port is substantially aligned with the dispensing port, and a second position, in which the outlet port is substantially out of alignment with the dispensing port. An analytical sample may be introduced into the reaction chamber through a closeable inlet means which communicates with the reaction chamber. In order to provide a substantially airtight, hermetic seal between the reaction chamber and the outside environment when the inlet into the reaction chamber is closed and the outlet means and the dispensing port are moved out of alignment, sealing means are provided between the insert member and the body. The insert member may include a generally cylindrical mating member adapted to be slidably and rotatably received in a corresponding generally cylindrical recess in the body. The container of the present invention may also be used to practice a method of processing an analytical sample, as will be described more fully hereinafter.

The foregoing features and advantages of the present invention will be more readily understood upon consideration of the following detailed description, taken in conjunction with the accompanying drawings, in which:

BRIEF DESCRIPTION OF DRAWINGS

FIG. 4 is a sectional view of the sample container showing the sample being held in the reaction chamber;

FIG. 5 is a view similar to that of FIG. 4, showing the addition of reagents through an auxiliary access port into the reaction chamber;

FIG. 6 is a view similar to that of FIG. 4, showing how the auxiliary access port may be hermetically sealed after the addition of reagents;

FIG. 7 is a top view of the sample container taken along the line 7—7 in FIG. 4, showing how the insert member may be rotated within the container body;

FIG. 8 is a view similar to that of FIG. 4, showing how the sample and reaction mixture may be dispensed from the container through a dispensing port.

DETAILED DESCRIPTION

Figure 1:
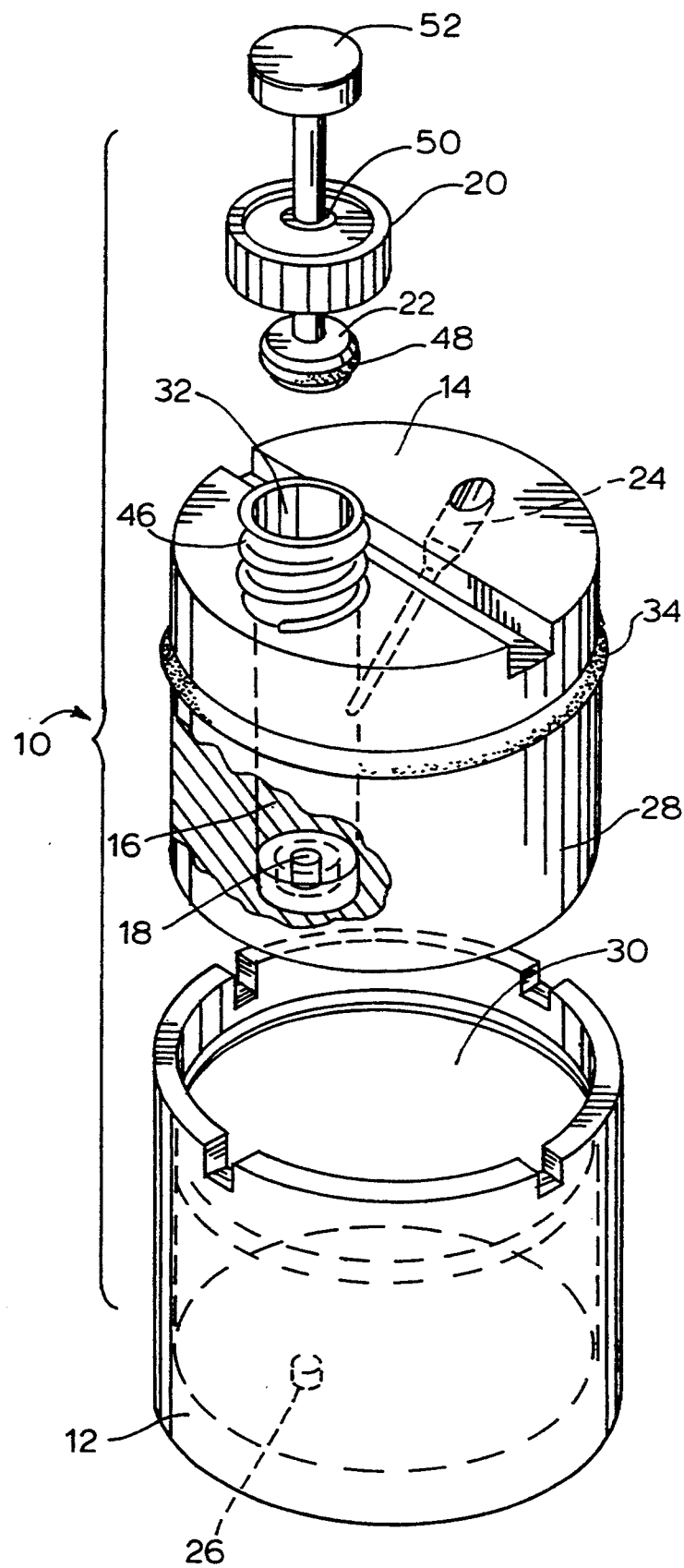
FIG. 1 is an exploded perspective view of a sample container made in accordance with the present invention.
Figure 2:
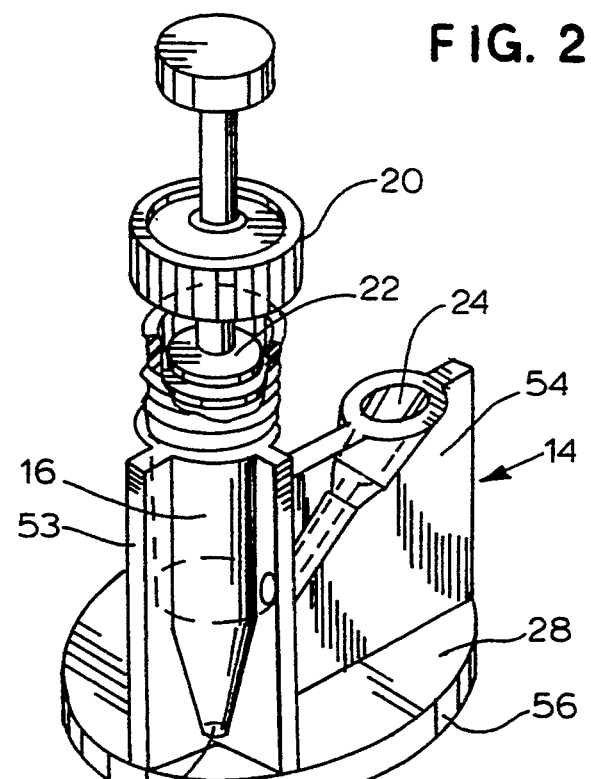
FIG. 2 is a perspective view of an alternative embodiment of the sample container made in accordance with the present invention.

FIGS. 1 and 2 show the general arrangement of a sample container 10 made in accordance with the present invention. This Specification describes a preferred form of the invention, in which the sample container is used to hold an analytical sample and contain the process of nucleic acid amplification. However, it will be understood that the container may be used to perform any of various processing steps commonly performed on analytical samples and well known to those skilled in the art. Such processing steps include, by way of example, chemical and immunochemical reactions, labelling and detection, and the like.

As best seen in FIG. 1, in general the container 10 includes a body 12 and an insert member 14 adapted to be received within the body 12. The insert member 14 includes a reaction chamber 16 in which the sample and any added reagents are held during sample handling and processing. A threaded cap and slidable plunger 22 may be used to close the inlet into the reaction chamber 16. Likewise, an auxiliary port 24, which communicates with the reaction chamber 16, may be provided for the addition of the sample and/or other reagents during processing. The container 10 is constructed so that the reaction chamber may be completely sealed from the outside environment during sample processing. Such an arrangement is particularly useful in helping to prevent sample and reagent cross-contamination when performing nucleic acid amplification reactions.

By aligning an outlet port 18 from the reaction chamber 16 with a dispensing port 26 on the body 12, fluids may be dispensed from the reaction chamber 16 for further processing and/or disposal. For example, after amplification reactions have taken place, aliquots of sample containing the amplified target may be transferred to a microtitre well for detection using conventional diagnostic methods. This dispensing step is preferably performed in a location remote from that where the amplification reaction takes place so that contamination of subsequent samples from aerosols that may be created during dispensing is avoided.

The container of the present invention may be used as part of an automated or semi-automated instrument designed to handle and process analytical samples. Such an instrument could be adapted to perform some or all of the steps described hereinafter, including manipulating the various components of the sample container.

If the container is used in an automated or semi-automated instrument, the container could be manually or mechanically moved to a remote position before the outlet port and dispensing port are rotated into alignment for dispensing.

Referring again to FIG. 1, the construction and operation of the container 10 will now be described in further detail. The basic components of the container are the body 12 and the insert member 14. In a preferred form of the invention, these components are molded from suitable plastics using conventional injection molding techniques. However, it will also be understood that other methods of manufacture may also be used. For example, the components could be molded by other means or they could be machined or formed from other well known plastics or materials.

To date, success has been had with a clear polycarbonate known as Lexan®, made by General Electric Co. In this regard, it is preferred that the material be optically transparent so that the laboratory technician may view the processes taking place in the reaction chamber. In addition, since a number of amplification reactions (in particular, 3SR) require that the sample be cycled through extremes of temperature, the container is preferably designed to withstand temperatures exceeding 100° C. without dimensional changes exceeding design requirements. Other materials which are preferred in the manufacture of the components include polypropylene—which is commonly used to manufacture vessels for containing amplification reactions—or other appropriate FDA-approved medical grade plastics.

The insert member 14 is designed to be slidably received in the body 12. In a preferred configuration, the insert member 14 has an integrally formed, generally cylindrical mating member 28 which is sized to fit in a corresponding generally cylindrical recess 30 in the body. Once inserted, the insert member 14 is free to rotate relative to the body about an imaginary vertical line passing through the center of cylindrical mating member 28. It will be understood, however, that other configurations which permit the insert member and body to slide relative to each other may be used. In this regard, it is not essential that the mating member and recess be generally cylindrical as long as they are adapted for relative movement.

Figure 9:
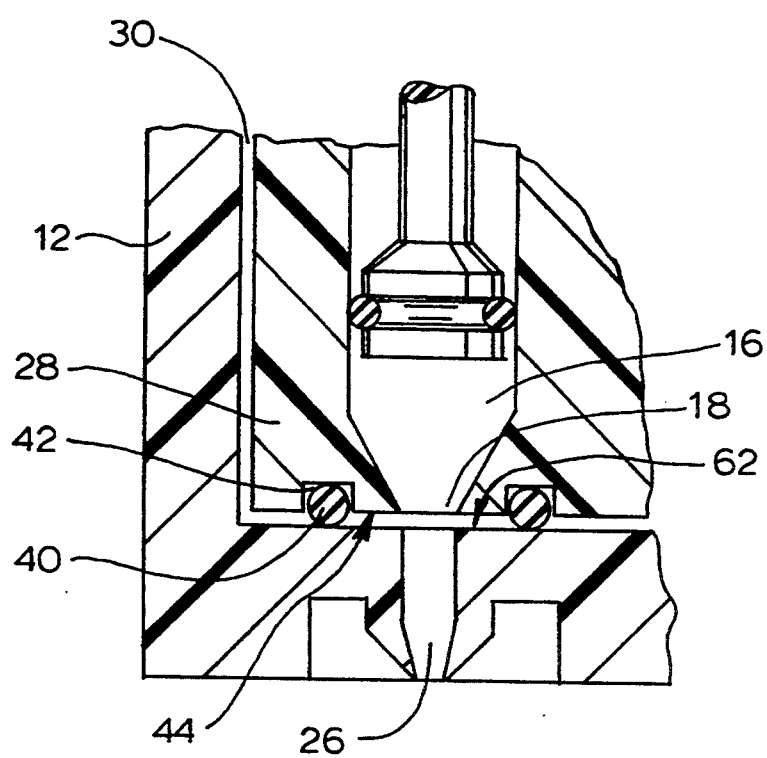
FIG. 9 is an enlarged cross-sectional view of a portion of the container, showing the reaction chamber outlet port axially aligned with the body dispensing port.

A reaction chamber 16 is formed in the insert member 14 by molding, forming, drilling, or the like. The reaction chamber may also be an insert which is made separately and then inserted into an appropriate aperture in the insert member. In that event, the reaction chamber insert may be made of the same or a different material as the other components of the container. A particularly preferred material for an insert of this type is polypropylene. In one form of the invention, the reaction chamber is smooth-walled and generally cylindrical in shape with a conical taper adjacent the outlet port. As best seen in FIGS. 2 and 9, in this arrangement, the reaction chamber 16 tapers to a smaller diameter, which is sized to closely match the upper diameter of the dispensing port 26 formed or drilled in the body, thereby facilitating smooth fluid flow through the aligned ports. In an alternative embodiment, the reaction chamber has two tapers, with the diameter of the chamber decreasing to form a narrower cylindrical region below the higher taper. In this arrangement, the slidable plunger may be designed so that it fits snuggly in the narrower cylindrical region beneath the first taper. However, as described in greater detail below, the chamber may be formed in any number of shapes, including rectangular, conical, or irregular. Indeed, as is also described in greater detail below, the container may be designed so that the reaction chamber actually changes in size and/or shape during the course of processing the sample.

The reaction chamber is preferably designed to contain an analytical sample during the processes of nucleic acid amplification; however, it will be understood that it may be shaped to hold the sample during any desired handling or processing step used in diagnostic methods. In a preferred form, the reaction chamber is designed to adequately contain the amount of fluid typically handled during amplification reactions—typically between about 20 $\mu$l and about 150 $\mu$l and, more particularly, between about 40 $\mu$l and about 103 $\mu$l of fluid. However, it will be understood that the chamber may be designed to hold any desired quantity of fluid.

The reaction chamber 16 is also preferably equipped with an inlet 32 and an outlet port 18. By rotating the insert member 14 relative to the body, the outlet port 18 may be brought substantially into or out of alignment with the dispensing port 26. Of course, it will be understood that this relative movement between the body and the insert member may be accomplished by holding the insert member still and moving the body, holding the body still and moving the insert member, or moving both simultaneously. Accordingly, references herein to "movement" or "rotation" of the insert member, mating member, or the body should be understood to include any means by which such relative movement is accomplished. When the outlet port 18 is moved to a first position, in which it is substantially aligned or communicating with the dispensing port 26, fluid may be dispensed from the reaction chamber 16 for further processing.

An inlet 32 may be used to introduce sample and/or reagents into the reaction chamber 16. In one preferred form of the invention, a closure means in the form of a threaded, sealed cap 20 can be used to close the inlet 32 in a substantially airtight manner. However, it will be understood that other conventional closure means may also be used, such as, by way of example, a septum, a self-sealing septum, a snap-fitable lid, or simply a plunger with a radial seal. It is also preferred that the reaction chamber be equipped with an auxiliary port 24 which communicates with the reaction chamber 16 at some point along its length. Such a port may be drilled or otherwise formed (e.g., by molding) in the insert member. When an auxiliary port is provided, it is preferred that the opening from the auxiliary port to the reaction chamber be as close to the bottom of the reaction chamber as possible, while still leaving sufficient volume to contain the sample/reagent solution. It is also preferred that the interior walls of this port be as smooth as possible to facilitate flow of reagents.

In the embodiment depicted in FIG. 1, this auxiliary port 24 is formed so that it passes at an angle from the top of the insert member 14 into the reaction chamber.

This angle should be sufficiently steep to permit fluid in the auxiliary port to flow readily under the influence of gravity into the reaction chamber; preferred angles are between about 35 and 80 degrees from horizontal and, more particularly, about 60 degrees from horizontal. This auxiliary port may be used to introduce sample and/or reagents into the reaction chamber 16. In a preferred form of the invention, this auxiliary port 24 is used to introduce reagents used to perform nucleic acid amplification reactions into the reaction chamber.

An important aspect of the present invention is the ability to seal the reaction chamber 16 in a substantially hermetic, airtight manner from the outside environment during and after the various sample-processing steps. This is particularly important to prevent contamination when performing nucleic acid amplification reactions; however, it will be understood that it is often desirable in other diagnostic procedures to isolate the sample and/or reagents from the outside environment during various processing steps.

This isolation or sealing may be accomplished in a number of ways. In one form of the invention, the container is provided with a plurality of sealing means. The first sealing means may take the form of a radial seal, such as an O-ring 34. The O-ring may be made of any appropriate elastomer, such as EPDM, for example, or of rubber. The O-ring 34 is affixed around the outer circumference of the mating member 28 so that it can create an airtight seal. As best seen in FIG. 4, in a preferred form of the invention this O-ring 34 is inserted into a circumferential groove 36 formed in the outer wall of the mating member 28. Insertion of the O-ring may be accomplished manually by stretching the elastomeric O-ring around the mating member 28 in an interference fit relationship or by insert molding the O-ring into the groove as part of an injection molding process. It will also be understood that other radial-type sealing means may be used, including u-cup shaped seals, gaskets, and the like.

Referring simultaneously to FIGS. 1 and 4, the O-ring is sized so that when the mating member 28 is inserted into the interior of the cylindrical recess 30 formed in the body 12, the O-ring will engage the interior wall of the cylindrical recess 30 in an interference fit relationship, thereby effecting a substantially airtight, hermetic seal between the side walls of the mating member 28 and the interior wall of the body 12.

Referring again to FIG. 1, a dispensing port 26 is formed or drilled in the body for dispensing fluid from the reaction chamber 16 when the outlet port 18 is rotated into alignment with the dispensing port 26. Since this dispensing port 26 communicates with the outside environment, a second sealing means is provided to isolate the outlet port 18 of the reaction chamber 16 from the dispensing port 26 when the ports are out of alignment.

The configuration of this second sealing means is best seen by reference to FIG. 9. This sealing means takes the form of a second O-ring 40. Success has been had with an O-ring bearing the designation AS-568-020, manufactured by Apple Rubber Products. This second O-ring 40 is affixed to a corresponding O-shaped recess 42 formed in the bottom wall 44 of the mating member 28 in the manner described above. When the mating member 28 is inserted into the cylindrical recess 30 formed in the body 12, the second O-ring 40 is pressed into engagement with the bottom wall of the cylindrical recess 30 to effect an airtight, hermetic seal when the outlet port 18 of the reaction chamber 16 is moved out of alignment with the dispensing port 26. (The outlet port 18 and dispensing port 26 are shown in alignment in FIG. 9; FIG. 4 illustrates the outlet port 18 and dispensing port 26 in an out-of-alignment position.) It will be understood that it may be necessary to press or force the second O-ring 40 into a sealing engagement with the bottom wall of the cylindrical recess 30 to effect the necessary seal. This may be accomplished either by applying a continuous downward force to the mating member 28 or by locking the mating member 28 to the body 12 so that the second O-ring is held in sealing engagement with the bottom wall of the recess 30.

Since the mating member 28 is received within the body 12, it will be seen that fluid held within the reaction chamber 16 will come into contact with the inner bottom wall 62 of the body 12. This is not undesirable, since such fluid may help to lubricate the second O-ring 40 and thereby assist in maintaining a substantially airtight seal. However, it will also be seen that when the mating member 28 is rotated relative to the body 12, fluid will be deposited along the inner bottom wall 62. Since this fluid could conceivably pass beyond the second O-ring, it is important that the first O-ring (identified by reference numeral 34 in FIG. 1) be present to provide a further barrier against release of the contents, which can result in contamination of the laboratory environment. It is also important that relative movement of the mating member 28 and the body be kept to a minimum before and during the amplification reaction so that fluid deposited on the inner bottom wall 62 does not pass beyond the second O-ring where it could be exposed to the outside environment through the dispensing port formed in the bottom of the body. Indeed, it is preferred that the mating member and body be kept in the same relative position during the addition of amplification reagents and during the entirety of the amplification reaction; movement should only occur in order to align the outlet port and the dispensing port for the dispensing step.

It should also be understood that the position and configuration of the sealing means in the drawings and accompanying description is exemplary only. In this regard, it will be apparent that additional sealing means could be used, and that the sealing means could be affixed to the body, rather than the insert member.

Referring again to FIG. 1, means are also provided to seal or close the inlet 32 into the reaction chamber 16 from the outside environment. This closure means may take the form of a threaded cap 20 which engages corresponding threads 46 on the top of the insert member 14. In a still further preferred form of the invention, the cap 20 is equipped with an associated plunger 22 adapted to be slidably received within the reaction chamber 16. Success has been had with a plunger made of Delrin ®, an acetal. The plunger 22 passes through a seal 50 in the cap 20 to prevent leakage. The plunger is also equipped with one or more circumferential elastomeric sealing lobes 48 sized and shaped to be inserted into the reaction chamber in an interference fit relationship, thereby further sealing the reaction chamber 16 from the outside environment. It will also be understood that other closure or sealing means may be used to close the inlet, such as, by way of example, a septum, a self-sealing septum, or a plunger with a radial seal but without an associated cap. In this regard, the use of a capless plunger simplifies the container and makes it possible to manufacture the container more easily and inexpensively.

The container may be equipped with one or more auxiliary ports 24, as shown in FIG. 1. In that event, the plunger 22 may serve an additional purpose. By pressing on the plunger handle 52, the plunger 22 can be moved downwardly into the reaction chamber 16. (It will be understood that in referring to this embodiment the term "reaction chamber" is used to mean the volume below the plunger seal. Accordingly, the reaction chamber actually decreases in volume as the plunger 22 is moved downwardly.) When the plunger 22 is moved below the level where the auxiliary port 24 makes entry into the reaction chamber 16, the plunger 22 effects a seal between the reaction chamber 16 and the auxiliary port 24 such that there is no longer communication between the two. When this is done, and the outlet port 18 is in a position out of alignment with the dispensing port 26 on the body, a substantially airtight seal is created between the reaction chamber 16 and the outside environment. As noted above, this is the preferred containment environment for performing many diagnostic procedures, especially nucleic acid amplification reactions.

Figure 3:
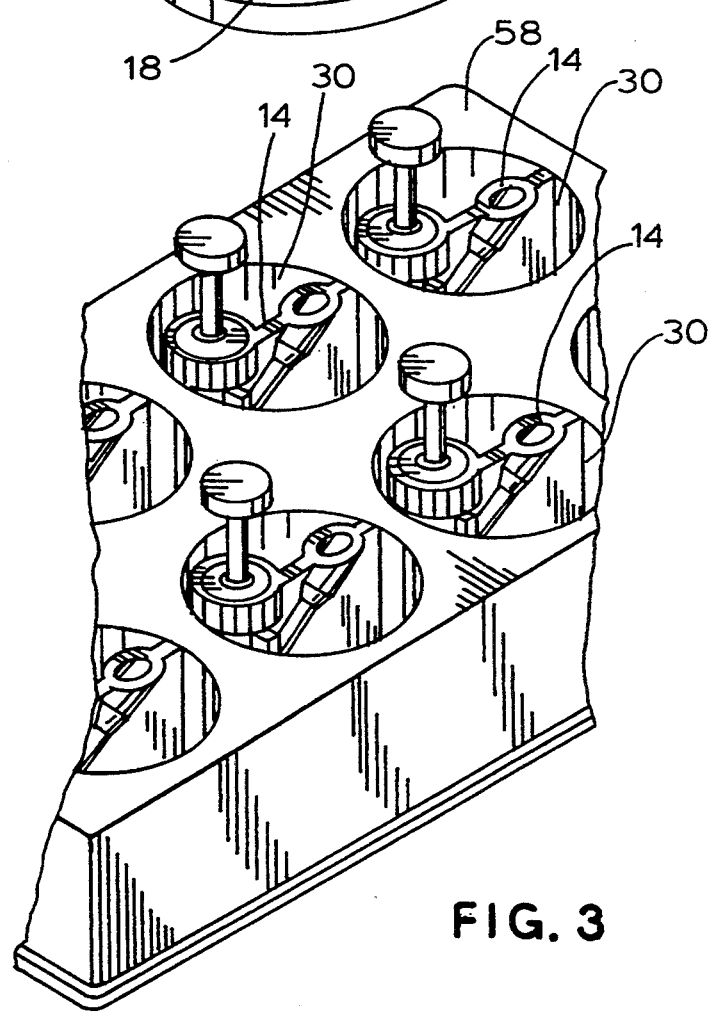
FIG. 3 is a view similar to that of FIG. 2 showing a plurality of sample containers held in a tray configuration.

FIGS. 2 and 3 illustrate an alternative embodiment of the present invention. In this embodiment, the container is designed in order to eliminate much of the material needed to manufacture the embodiment illustrated in FIGS. 1 and 4-9. This is desirable for a number of reasons. First, a reduction in the amount of material reduces the overall cost of manufacturing the container. Second, a reduction in material makes it easier to rapidly and efficiently heat and cool the reaction chamber and its contents. This is particularly important when performing amplification reactions (and, in particular, 3SR), since it is often necessary to take the sample and/or reagents through cyclical temperature changes. Preferably, a reduced-material design is created by injection molding, as described above.

Referring now to FIG. 2, it will be seen that in this embodiment the insert member 14 is no longer a solid cylindrical block. As a result, the generally cylindrical mating member 28 is greatly reduced in size. The reaction chamber 16 is formed in the insert member 14 and is supported by a plurality of struts 53 molded around its periphery. Similarly, the auxiliary port 24 is formed in an integral upright wall 54 of the insert member 14.

The reaction chamber 16 is sealed from the outside environment in a manner similar to that described above. A first sealing means in the form of an O-ring or other radial seal (not shown in FIG. 3) may be affixed in a manner similar to that described above to the outer cylindrical wall 56 of the mating member 28 to engage the inner wall of the body in an interference fit relationship. Likewise, a second sealing means in the form of a second O-ring (not shown) may be affixed to the bottom wall of the mating member surrounding the periphery of the outlet port 18 to effect a face seal between the outlet port 18 and the bottom of the cylindrical recess in the body, as described above. A cap 20 and associated plunger 22 may also be provided as described above to seal the inlet into the reaction chamber 16 and, on moving the plunger 22 downward, to close the auxiliary port.

FIG. 3 illustrates a "cartridge" for holding a plurality of containers. In this embodiment, a plurality of insert members 14 are inserted into corresponding cylindrical recesses 30 in tray 58. The bottom of tray 58 is equipped with a dispensing port (not shown) for each insert member 14. In this way, a plurality of samples may be processed in separate containers at the same time—an important advantage in most diagnostic procedures, particularly those performed in clinical and hospital laboratories.

FIGS. 4–8 illustrate the sequence of steps which may be followed in using the container of the present invention to hold and process an analytical sample. In the description which follows, it will be assumed that a nucleic acid amplification reaction will be performed on the sample; however, as noted above, it will be understood that the container may also be used to perform other diagnostic procedures in which isolation from the outside environment is desired.

Prior to the introduction of sample and/or initial reagents into the container, the mating member 28 is rotated to a position in which the outlet port 18 of the reaction chamber 16 is substantially out of alignment with the dispensing port in the body. FIG. 4 illustrates the container after the sample and initial reagents 60 have been placed in the reaction chamber 16. Generally, the initial reagents include lysing agents which break down the cell membranes or protein coatings of the sample, thereby releasing nucleic acids from the sample so that they may be amplified. The sample and lysing reagents may be introduced into the reaction chamber by removing the threaded cap 20 and associated plunger 22 and pipetting or otherwise transporting the sample and reagents through the inlet 32, or by piercing a sealed septum covering the inlet with a needle or probe. Alternatively, the lysing reagents may be stored in the reaction chamber in a dried or lyophilized form prior to introduction of the sample and then reconstituted upon addition of sample. In total, approximately 40 $\mu$l of sample and lysing reagents are present when performing 3SR amplification.

In a step which is not shown in the drawings, immediately after the sample and/or initial reagents are added, the plunger is moved downwardly below the level of the auxiliary port, thereby closing it from communication with the reaction chamber. This helps to immediately isolate the sample from the outside environment, thereby reducing contamination problems. It will also be understood that the auxiliary port may also be closed by other means, including a separate valve, for example. Of course, if no auxiliary port is provided, this step is unnecessary.

To prepare the sample for the addition of amplification reagents, the sample may be subjected to temperature cycling. For example, when 3SR amplification is used, the container (or cartridge containing a plurality of containers) may be placed in an incubator, where the sample is first heated to a temperature of 50° C. for about 60 minutes, then to 100° C. for approximately 5 minutes, and finally to 42° C. prior to addition of 3SR amplification reagents. It will be understood that other temperature conditions well known to those skilled in the art may be necessary for other amplification reactions.

FIG. 5 illustrates the addition of amplification reagents through the auxiliary port 24. In a step which occurs prior to that shown in FIG. 5, the reagents to be added are conveyed into the auxiliary port while the plunger is still in its lowered position covering or closing the opening 23 which leads from the auxiliary port into the reaction chamber. The plunger 22 thereby prevents communication between the auxiliary port and the reaction chamber. It will be understood, however, that these reagents may also be added through the inlet 32 if no auxiliary port is provided. For example, the reagents could be added by removing the cap 32 or by piercing a self-sealing septum covering the inlet with a needle or probe.

When one or more auxiliary ports are provided, the amplification reagents are transported by pipette or other means, either manually or robotically, into the auxiliary port 24. For 3SR amplification, the amplification reagents or "cocktail" may include, by way of example, buffers, rNTP's and dNTP's, primers, and other reagents. As shown in FIG. 5, the plunger 22 is then raised above the opening 23 in the auxiliary port 24 so that reagents are allowed to pass under the influence of gravity in the direction of the arrows and into the reaction chamber 16. To maintain a condition in which the reaction chamber is sealed from the outside environment during this step, it is preferred that the reagents be pipetted through the auxiliary port 24 in appropriate quantities so that the reaction chamber 16 is actually sealed from the outside environment by the fluid passing through the auxiliary port 24 until the auxiliary port may be closed or sealed mechanically, as described below. It is also important that the plunger 22 be raised only long enough for the appropriate metered quantity of reagents to pass into the reaction chamber. Finally, it is important that the level of the sample/reagent mixture not be permitted to rise to the level of the auxiliary port opening into the reaction chamber, where it potentially could be exposed to the outside environment during later processing steps.

FIG. 6 illustrates the next step in the preferred sequence. After the appropriate metered quantity of reagents is allowed to pass into the reaction chamber, and while the fluid seal is being maintained in the auxiliary port 24 by the amplification reagents, the plunger handle 52 is once again depressed to move the plunger 22 downward in the direction of the arrow in FIG. 6. It will be understood that movement of the plunger may be accomplished manually by the laboratory technician or mechanically by means of an automated or semi-automated instrument equipped to mechanically raise and lower the plunger 22 during the various raising and lowering motions described herein. The plunger 22 is moved downwardly past the opening from the auxiliary port into the reaction chamber 16. The lobe 48 on the plunger 22 thereby once again seals or closes the auxiliary port 24 from communicating with the reaction chamber, which, after the plunger is lowered, is the decreased volume located beneath the lobe 48. At this point, with the mating member 28 positioned such that the outlet port 18 is out of alignment or communication with the dispensing port on the body, the reaction chamber 16 is substantially isolated from the outside environment by an airtight, hermetic seal created by the first O-ring 34, the second O-ring 40, the lobe 48 on the plunger, and the threaded cap 20. The amplification reaction may thus proceed in a completely sealed chamber, thereby significantly reducing the possibility that nucleic acids from other sources will contaminate the sample and interfere with diagnostic test results, or that amplified nucleic acids will be released from the container into the surrounding laboratory environment.

FIG. 7 illustrates the next step in the preferred sequence. After the amplification reaction is complete, the sample now includes amplified quantities of the target sequence (assuming, of course, that the target was present in the sample to begin with). To help reduce the possibility that amplified target will be released in the location where other samples will be subjected to amplification, it is now desirable to transfer the container to another location in order to perform one or more assays for the amplified target. Typically, the container will be transferred to another location where the sample can be dispensed into a microtitre well or other similar analytical vessel. Here it will be subjected to various labelling and detection reactions so that the presence or absence of the target may be detected. Problems associated with exposing the sample to the outside environment are greatly reduced if detection is performed in a remote location designed to inhibit movement of any aerosols back toward the amplification zone (e.g., by means of a positive airflow system).

In order to permit the sample to be dispensed from the container, the mating member 28 is rotated relative to the body 12 about an imaginary axis passing through the center of the cylindrical mating member 28. (This imaginary axis is indicated by an "x" in FIG. 7 and by the dotted lines in FIGS. 4-6.) The mating member 28 is moved or rotated in this manner until the outlet port of the reaction chamber is brought into alignment with the dispensing port on the body. As noted above, this may be accomplished by any means which moves the mating member 28 relative to the body 12. As with actuation of the plunger, the components may be moved either manually by an operator or mechanically in an automated or semi-automated instrument designed to grip one or more of the components. At this point, sample held within the reaction chamber may be dispensed through the outlet port and dispensing port.

FIG. 8 illustrates the use of the plunger 22 to dispense the sample out of the container. Once the outlet port 18 is aligned with the dispensing port 26, downward movement of the plunger 22 in the direction of the arrow in FIG. 8 moves the sample by controlled, positive displacement out of the ports. By sizing and shaping the ports appropriately, downward incremental movement of the plunger 22 can be correlated to precise metered quantities of the sample solution being expelled or discharged from the ports. For many diagnostic procedures, it is preferred that the solution be dispensed in single or multiple increments of 10-15 $\mu$l and, more preferably, about 10 $\mu$L. For this purpose, the plunger may be depressed the correct incremental distances either manually or automatically. It will also be understood that the sample solution may be permitted to exit under the influence of gravity alone or may be expelled by other well-known dispensing mechanisms.

After dispensing is complete, the mating member may be rotated again to position the outlet port and the dispensing port so that they are out of alignment. In this way, the contents of the reaction chamber are sealed, preventing leakage and potential biohazard. The sealed container may then be disposed of in an appropriate fashion.

While the invention has been described in connection with certain presently preferred components and arrangements, those skilled in the art will recognize many modifications to structure, arrangement, portions, elements, materials, steps, and components which can be used in the practice of the invention without departing from the principles thereof.

What is claimed is:

1. A container for holding an analytical sample during processing comprising:

a body having a dispensing port, an insert member slidably received in the body, said insert member defining a reaction chamber with (a) a closeable inlet means communicating with the reaction chamber for introducing an analytical sample into the reaction chamber, and (b) an outlet port, said insert member and said body being movable relative to each other between a first position, in which the outlet port of the reaction chamber is substantially aligned with the dispensing port of the body, and a second position, in which the outlet port of the reaction chamber is substantially out of alignment with the dispensing port of the body, sealing means located between the insert member and the body for providing a substantially airtight seal between the reaction chamber and the outside environment when the insert member and body are in the second position and the inlet means is closed; and an auxiliary port in the insert member, said auxiliary port communicating with the reaction chamber, and valve means cooperating with the auxiliary port for closing the auxiliary port.

2. A container for holding an analytical sample during processing comprising:

a body having a dispensing port and a generally cylindrical recess formed therein, an insert member, said insert member including a generally cylindrical mating member slidably and rotatably received in the cylindrical recess in the body, said insert member further defining a reaction chamber having an inlet port, an auxiliary port, and an outlet port, each of said inlet, auxiliary, and outlet ports communicating with the reaction chamber, said mating member and said body being rotatable relative to each other between a first position, in which the outlet port of the reaction chamber is substantially aligned with the dispensing port of the body, and a second position, in which the outlet port of the reaction chamber is substantially out of alignment with the dispensing port of the body, first sealing means located between the mating member and the recess in the body for maintaining a substantially airtight seal therebetween, second sealing means located between the outlet port of the reaction chamber and the dispensing port of the body for maintaining a substantially airtight seal therebetween, valve means cooperating with the auxiliary port of the reaction chamber for closing the auxiliary port, closure means cooperating with the inlet port of the reaction chamber for closing the inlet port, said first and second sealing means and said valve and closure means providing a substantially airtight seal between the reaction chamber and the outside environment when the mating member and body are in the second position and the valve and closure means are in their closed conditions, and dispensing means coupled to said reaction chamber for dispensing fluids from the reaction chamber through the outlet port of the reaction chamber and the dispensing port of the body when the mating member and body are in the first position.

3. A method of processing an analytical sample comprising:

providing a container for holding an analytical sample said container comprising a body having a dispensing port, an insert member slidably received in the body, said insert member defining a reaction chamber with (a) a closeable inlet means communicating with the reaction chamber for introducing an analytical sample into the reaction chamber, and (b) an outlet port, said insert member and said body being movable relative to each other between a first position, in which the outlet port of the reaction chamber is substantially aligned with the dispensing port of the body, and a second position, in which the outlet port of the reaction chamber is substantially out of alignment with the dispensing port of the body, and sealing means located between the insert member and the body for providing a substantially airtight seal between the reaction chamber and the outside environment when the insert member and the body are in the second position and the inlet means is closed:

positioning the insert member and the body in the second position;

introducing an analytical sample into the reaction chamber through the inlet means;

introducing sample-processing reagents into the reaction chamber through the inlet means:

closing the inlet means:

positioning the insert member and the body in the first position; and dispensing the sample and reagents from the reaction chamber;

wherein the container further comprises an auxiliary port in the insert member, said auxiliary port communicating with the reaction chamber, and valve means cooperating with the auxiliary port for closing the auxiliary port, and wherein additional sample-processing reagents are introduced into the reaction chamber through the auxiliary port after which the auxiliary port is then closed by the valve means.

4. A method of processing an analytical sample comprising:

providing a container for holding an analytical sample, said container comprising a body having a dispensing port and a generally cylindrical recess formed therein, an insert member, said insert member including a generally cylindrical mating member slidably and rotatably received in the cylindrical recess in the body, said insert member further defining a reaction chamber having an inlet port, an auxiliary port, and an outlet port, each of said inlet, auxiliary, and outlet ports communicating with the reaction chamber, said mating member and said body being rotatable relative to each other between a first position, in which the outlet port of the reaction chamber is substantially aligned with the dispensing port of the body, and a second position, in which the outlet port of the reaction chamber is substantially out of alignment with the dispensing port of the body, first sealing means located between the mating member and the body for maintaining a substantially airtight seal therebetween, second sealing means located between the outlet port of the reaction chamber and the dispensing port of the body for maintaining a substantially airtight seal therebetween, valve means cooperating with the auxiliary port of the reaction chamber for closing the auxiliary port, closure means cooperating with the inlet port of the reaction chamber for closing the inlet port, said first and second sealing means and said valve and closure means providing a substantially airtight seal between the reaction chamber and the outside environment when the mating member and body are in the second position and the valve and closure means are in their closed conditions, and dispensing means coupled to said reaction chamber for dispensing fluids from the reaction chamber through the outlet port of the reaction chamber and the dispensing port of the body when the mating member and body are in the first position;

positioning the mating member and the body in the second position;
introducing an analytical sample into the reaction chamber through the inlet port;
closing the inlet port with the closure means;
introducing sample-processing reagents into the reaction chamber through the auxiliary port;
closing the auxiliary port with the valve means;
positioning the mating member and body in the first position; and
actuating the dispensing means to dispense the sample and the reagents from the reaction chamber.

* * * * *